United States Patent [19]
Srivastava

[11] Patent Number: 5,997,873
[45] Date of Patent: Dec. 7, 1999

[54] METHOD OF PREPARATION OF HEAT SHOCK PROTEIN 70-PEPTIDE COMPLEXES

[75] Inventor: Pramod K. Srivastava, Riverdale, N.Y.

[73] Assignee: Mount Sinai School of Medicine of the City University of New York, New York, N.Y.

[21] Appl. No.: 08/180,685

[22] Filed: Jan. 13, 1994

[51] Int. Cl.$^6$ ................. A61K 39/385; A61K 38/02; A01N 37/18; A23J 1/00

[52] U.S. Cl. .................. 424/193.1; 424/195.11; 424/196.11; 424/197.11; 424/277.1; 424/278.1; 530/412; 530/413; 530/828; 514/2; 514/21

[58] Field of Search .................. 424/277.1, 278.1, 424/193.1, 195.11, 196.11, 197.11; 530/412, 413, 828; 514/21, 2

[56] References Cited

U.S. PATENT DOCUMENTS

| | | |
|---|---|---|
| 4,690,915 | 9/1987 | Rosenberg . |
| 5,188,964 | 2/1993 | McGuire et al. . |
| 5,232,833 | 8/1993 | Sanders et al. . |
| 5,348,945 | 9/1994 | Berberian et al. .................. 514/21 |

FOREIGN PATENT DOCUMENTS

| | | |
|---|---|---|
| 196 02 985 A1 | 7/1997 | Germany . |
| 2 251 186A | 7/1992 | United Kingdom . |
| WO 89/12455 | 12/1989 | WIPO . |
| WO 90/02564 | 3/1990 | WIPO . |
| WO 91/15572 | 10/1991 | WIPO . |
| WO 92/01717 | 2/1992 | WIPO . |
| WO 92/08484 | 5/1992 | WIPO . |
| WO 92/08488 | 5/1992 | WIPO . |
| WO 93/14118 | 7/1993 | WIPO . |
| WO 93/17712 | 9/1993 | WIPO . |
| WO 93/18146 | 9/1993 | WIPO . |
| WO 93/18147 | 9/1993 | WIPO . |
| WO 93/18150 | 9/1993 | WIPO . |
| WO 93/21529 | 10/1993 | WIPO . |
| WO 93/24136 | 12/1993 | WIPO . |
| WO 94/11513 | 5/1994 | WIPO . |
| WO 97/06685 | 2/1997 | WIPO . |
| WO 97/06821 | 2/1997 | WIPO . |
| WO 97/06828 | 2/1997 | WIPO . |
| WO 97/26910 | 7/1997 | WIPO . |

OTHER PUBLICATIONS

Martin et al. (1986) "Role of Murine Tumor Models in Cancer Treatment Research", Cancer Res 46:2189–2192.

Mulé et al. (1984) "Adoptive Immunotherapy of Established Pulmonary Metastases with LAK Cells and Recombinant Interleukin–2", Science 225:1487–1489.

Srivastava et al. (Mar. 1993) "Evidence for peptide–chaperoning by the endoplasmic reticular heat shock protein GP96: Implications for vaccination against cancer and infectious diseases", J Cell Biochem Suppl 17D:94 (Abstract NZO14).

Thomas et al. (1982) "Molecular and Cellular Effects of Heat Shock and Related Treatments of Mammalian Tissue–Culture Cells", Cold Spring Harbor Symp Quant Biol 46:985–996.

Welch et al. (1982) "Purification of the Major Mammalian Heat Shock Proteins", J Biol Chem 257:14949–14959.

Levinson et al. (1979) "Metal Binding Drugs Induce Synthesis of Four Proteins in Normal Cells", Biol Trace Element Research 1:15–23.

Barrios et al., 1994, "Specificity of antibodies induced after immunization of mice with the mycobacterial heat shock protein of 65kD", Clin. Exp. Immunol., 98:224–228.

Barrios et al., 1994, "Heat shock protein as carrier molecules: in vivo helper effect mediated by *Escherichia coli* GroEL and DnaK proteins requires cross–linking with antigen", Clin. Exp. Immunol., 98:229–233.

Aldovini et al. (1992) "The New Vaccines", *Technology Review* pp. 24–31.

Bensaude et al. (1983) "Spontaneous high expression of heat–shock proteins in mouse embryonal carcinoma cells and ectoderm from day 8 mouse embryo", *EMBO J.* 2:173–177.

Blachere et al. (1993) "Heat Shock Protein Vaccines Against Cancer," *Journal of Immunotherapy* 14:352–356.

Blachere and Srivastava (1993) "Immunization with GP96 heat shock proteins isolated from tumors or influenza virus infected cells elicits MHC–restricted, antigen–specific cytotoxic T lymphocytes against the corresponding cells", *J. Cellular Biochem. Keystone Symposia* NZ502, p. 124.

Cohen (1993) "Cancer vaccines get a shot in the arm", *Science* 262:841–843.

Craig (1993) "Chaperones: Helpers Along the Pathways to Protein Folding", *Science* 260:1902–1904.

Elliot et al. (1990) "Naturally Processed Peptides", *Nature* 348:195–197.

Lussow, A.R. et al., "Mycobacterial heat–shock proteins as carrier molecules", Eur. J. Immunol. (1991), 21: 2297–2302.

Barrios, C. et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guérin priming", Eur. J. Immunol. (1992), 22: 1365–1372.

Prehn, R.T. and Main, J.M., "Immunity to Methylcnolanthrene–Induced Sarcomas", Journal of National Cancer Institute, Jun. 1957, vol, 18, No. 6, pp. 769–778.

Globerson, A. and Feldman, M., "Antigenic Specificity of Benzo[a]pyrene–Induced Sarcomas", Journal of National Cancer Institute, Jun. 1964, vol. 32, No. 6, pp. 1229–1242.

(List continued on next page.)

*Primary Examiner*—Paula K. Hutzell
*Assistant Examiner*—Geetha P. Bansal
*Attorney, Agent, or Firm*—Pennie & Edmonds LLP

[57] ABSTRACT

The present invention relates to methods of preparing a purified non-covalent heat shock protein 70-peptide complex capable of eliciting an immune response in a mammal comprising purifying heat shock protein 70-peptide complexes from mammalian tumor cells or mammalian cells infected with a virus, bacteria, or other infectious agent in the absence of ATP.

36 Claims, 6 Drawing Sheets

OTHER PUBLICATIONS

Ebert, E.C. et al., "Characterization of an immunosuppresive factor derived from colon cancer cells", The Journal of Immunology, Apr. 1, 1987, vol. 138, No. 7, pp. 2161–2168.

Mizoguchi, H. et al., "Alterations in signal transduction molecules in T lymphocytes from tumor–bearing mice", Science, Dec. 11, 1992, vol. 258, pp. 1795–1798.

Huber, D. et al., "Protease inhibitors interfere with the transforming growth factor–μ–dependent but not the transforming growth factor–μ–independent pathway of tumor cell–mediated immunosuppression", The Journal of Immunology, Jan. 1, 1992, vol. 148, No. 1, pp. 277–284.

Lukacs, K.V. et al., "Tumor cells transfected with bacterial heat–shock gene lose tumorigenicity and induce protection against tumors", J. Exp. Med., Jul. 1993, vol. 178, pp. 343–348.

Basombrío, Miguel Angel, "Search for common antigenicities among twenty–five sarcomas induced by methylcholanthrene", The Institute for Cancer Research, Oct. 1970, vol. 30, pp. 2458–2462.

Boon, Thierry, Toward a genetic analysis of tumor rejection antigens, Advances in Cancer Research, vol. 58, pp. 177–210.

Ullrich, S.J. et al., "A mouse tumor–specific transplantation antigen is a heat shock–related protein", Proc. Natl. Acad. Sci., May 1986, vol. 83, pp. 3121–3125.

Srivastava, P.K. and Heike, M., "Tumor–specific immunogenicity of stress–induced proteins: convergence of two evolutionary pathways of antigen presentation?", Seminars in Immunology (1991), vol. 3, pp. 57–64.

Srivastava, P.K. and Maki, R.G., "Stress–induced proteins in immune response to cancer", Microbiology and Immunology (1991), vol. 167, pp. 109–123.

Li Z. and Srivastava, P.K., "Tumor rejection antigen gp96/grp94 is an ATPase: implications for protein folding and antigen presentation", The EMBO Journal (1993), vol. 12, No. 8, pp. 3143–3151.

Lindquist, S. and Craig, E.A., "The heat–shock proteins", Annu. Rev. Genet. (1988), 22: 631–677.

Vanbuskirk, A. et al., "A peptide binding protein having a role in antigen presentation is a member of the hsp70 heat shock family", J. Exp. Med., Dec. 1989, vol. 170, pp. 1799–1809.

Flynn, G.C. et al., "Peptide–binding specificity of the molecular chaperone BiP", Nature, Oct. 24, 1991, vol. 353, pp. 726–730.

Van den Eynde, B. et al., "The gene coding for a major tumor rejection antigen of tumor P815 is identical to the normal gene of syngeneic DBA/2 mice", J. Exp. Med., June 1991, Vol. 173, pp. 1373–1384.

Fedweg, A.M. and Srivastava, P.K., "Evidence for biochemical heterogeneity of gp96 heat shock protein/tumor rejection antigen", Mount Sinai School of Medicine, NZ 206, p. 108.

Palladino, M.A., Jr. et al., "Expression of a shared tumor–specific antigen by two chemically induced BALB/c sarcomas", Cancer Research, Oct. 1, 1987, 47: 5074–5079.

Srivastava, P.K. et al., "Tumor rejection antigens of chemically induced sarcomas of inbred mice", Proc. Natl. Acad. Sci., Immunology, May 1986, vol. 83, pp. 3407–3411.

Flynn, G.C. et al., "Peptide binding and release by proteins implicated as catalysts of protein assembly", Science, Jul. 28, 1989, vol. 245, pp. 385–390.

Lakey, E.K. et al., "Identification of a peptide binding protein that plays a role in antigen presentation", Proc. Natl. Acad. Sci., Immunology, Mar. 1987, vol. 84, pp. 1659–1663.

Szikora, J.P. et al., "Structure of the gene of tum–transplantation antigen P35B presence of a point mutation in the antigenic allele", The EMBO Journal (1990), vol. 9, No. 4, pp. 1041–1050.

Falk et al. (1990) "Cellular Peptide Composition Governed by Major Histocompatibility Complex Class I Molecules", Nature 348:248–251.

Falk et al. (1991) "Allele–specific Motifs Revealed by Sequencing of Self–peptides Eluted from MHC Molecules", Nature 351:290–296.

Flynn et al. (1991) "Peptide–binding Specificity of the Molecular Chaperone BiP", Nature 353:726–730.

Franklin (1993) "Making vaccines fit the cancer", New Scientist 140:17.

Gething et al. (1992) "Protein Folding in the Cell", Nature 355:33–45.

Jakob et al. (1993) "Small Heat Shock Proteins Are Molecular Chaperones", J. Biol. Chem. 268:1517–1520.

Jardetzky et al. (1991) "Identification of Self Peptides Bound to Purified HLA–B27", Nature 353:326–329.

Lanzavecchia (1993) "Identifying Strategies for Immune Intervention", Science 260:937–944.

Lévy (1991) "ATP is Required for In Vitro Assembly of MHC Class I Antigens but Not for Transfer of Peptides across the ER Membrane", Cell 67:265–274.

Luescher et al. (1991) "Specific Binding of Antigenic Peptides to Cell–associated MHC Clas I Molecules", Nature 351:72–77.

Madden et al. (1990) "The Structure of HLA–B27 Reveals Nonamer Self–peptides Bound in an Extended Conformation", Nature 353:321–325.

Maki et al. (1990) "Human homologue of murine tumor rejection antigen gp96: 5'–Regulatory and coding regions and relationship to stress–induced proteins", Proc. Natl. Acad. Sci. USA 87:5658–5663.

Maki et al. (1993) "Mapping of the Genes for Human Endoplasmic Reticular Heat Shock Protein gp96/grp94", Somatic Cell Mol. Genetics 19(1):73–81.

McCall et al. (1989) "Biotherapy: A New Dimension in Cancer Treatment", Biotechnology 7:231–240.

Melnick (1985) "Virus Vaccines: An Overview", Proceedings of the First Annual Southwest Foundation for Biomedical Research International Symposium, Houston, Texas, Nov. 8–10, 1984, American Society for Microbiology pp. 1–13.

Mizoguchi et al. (1982) "Alterations in signal transduction molecules in T lymphocytes from tumor–bearing mice", Science 258:1795–1798.

Nelson et al. (1992) "The Translation Machinery and 70 kd Heat Shock Protein Cooperate in Protein Synthesis", Cell 71:97–105.

Rothman (1989) "Polypeptide Chain Binding Proteins: Catalysts of Protein Folding and Related Processes in Cells", Cell 59:591–601.

Rötzschke et al. (1990) "Isolation and Analysis of Naturally Processed Viral Peptides as Recognized by Cytotoxic T cells", Nature 348:248–251.

Salk et al. (1993) "A Strategy for Prophylactic Vaccination Against HIV", Science 260:1270–1272.

Schumacher et al. (1991) "Peptide Selection by MHC Class I Molecules", Nature 350:703–706.

Srivastava et al. (1984) "The Serologically Unique Cell Surface Antigen of Zajdela Ascitic Hepatoma is also its Tumor–Associated Transplantation Antigen", *Int. J. Cancer* 33:417–422.

Srivastava et al. (1987) "5'–Structural analysis of genes encoding polymorphic antigens of chemically induced tumors", *Proc. Natl. Acad. Sci. USA* 84:3807–3811.

Srivastava et al. (1988) "Chromosonal Assignment of the Gene Encoding the Mouse Tumor Rejection Antigen gp96", *Immunogenetics* 28:205–207.

Srivastava et al. (1988) "Individually Distinct Transplantation Antigens of Chemically Induced Mouse", *Immunology Today* 9:78–83.

Srivastava et al. (1989) "Identification of a Human Homologue of the Murine Tumor Rejection Antigen GP96," *Cancer Res.* 49:1341–1343.

Srivastava et al. (1991) "Protein Tumor Antigens", *Curr. Opin. Immunol.* 3:654–658.

Srivastava et al. (1993) "Peptide–Binding Heat Shock Proteins in the Endoplasmic Reticulum: Role in Immune Response to Cancer and in Antigen Presentation", *Advances in Cancer Research* 62:153–177.

Subbarao et al. (1992) "A General Overview of Viral Vaccine Development," *Genetically Engineered Vaccines* 327:51–57.

Udono (1993) "Heat shock proteins HSP70, HSP90 and GP96 elecit tumor specific immunity to the tumors from which they are isolated", *J. Cell. Biochem.* Suppl. 17D:113 (Abstract NZ225).

Udono et al. (1993) "Heat Shock Protein 70–associated Peptides Elicit Specific Cancer Immunity", *J. Exp. Med.* 178:1391–1396.

Viitanen et al. (1992) "Mammalian Mitochondrial Chaperonin 60 Functions as a Single Toroidal Ring", *J. Biol. Chem.* 267:695–698.

Welch et al. (1985) "Rapid Purification of Mammalian 70,000–Dalton Stress Proteins: Affinity of the Proteins for Nucleotides", *Mol. Cell. Biol.* 5:1229–1237.

Welch (1993) "How Cells Respond to Stress", *Scientific American* pp. 56–64.

Young (1990) "Stress Proteins and Immunology", *Annu. Rev. Immunol.* 8:401–420.

Yu et al. (1991) "Sequence Analysis of Peptides Bound to MHC Class II Molecules", *Nature* 353:622–627.

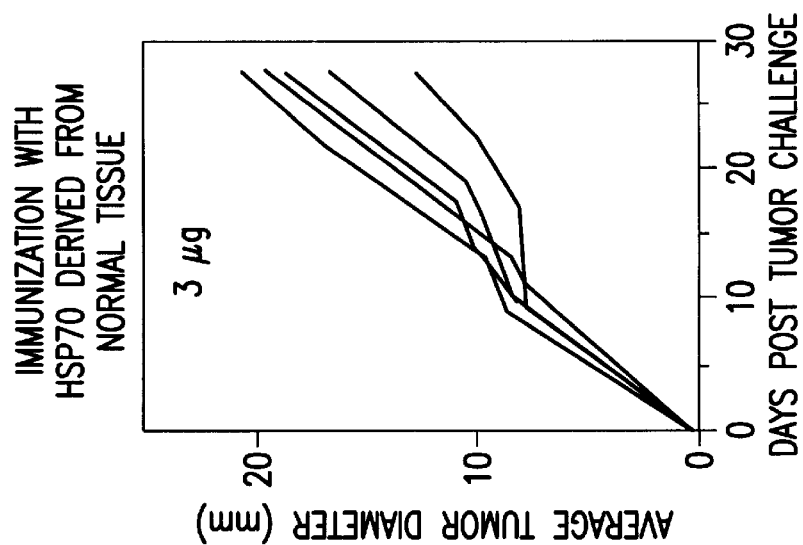
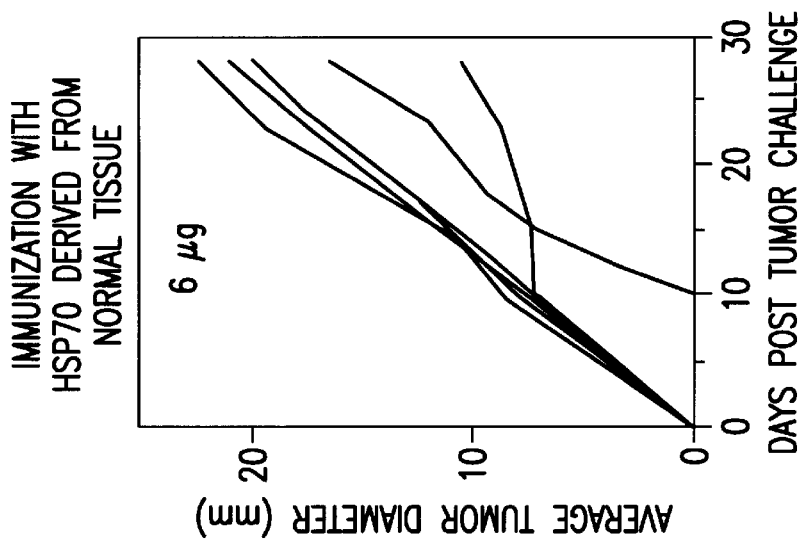
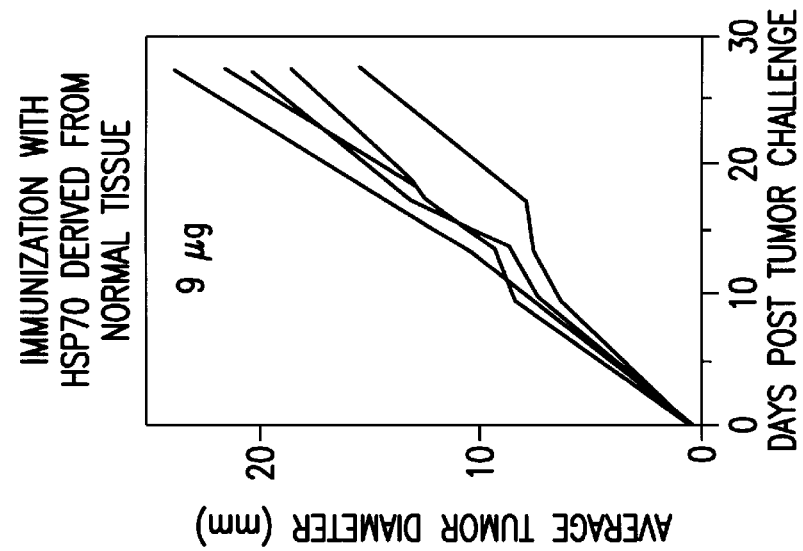

METHOD OF PREPARATION OF HEAT SHOCK PROTEIN 70-PEPTIDE COMPLEXES

This invention was made with Government support under National Institute of Health Grant No. CA44786 (GCO Project #88-416 PHA; Fund #G5-204X). The Government has certain rights in this invention.

FIELD OF THE INVENTION

This invention relates to a method of using heat shock protein 70 preparations obtained from tumor cells or cells infected with a virus or other agent in order to elicit an immune response against the tumor, virus or other agent.

BACKGROUND OF THE INVENTION

The observation that inbred mice and rats can be immunized against their own tumors or tumors of the same genetic background have led to a hypothesis that tumor-specific antigens exist. In essence, these studies showed that mice vaccinated with inactivated cancer cells are immune to subsequent challenges of live cancer cells. The phenomenon was shown to be individually tumor-specific, in that mice were immune specifically to the tumors used to immunize them and not to other tumors. The demonstration of immunogenicity of cancer cells led to a search for the cancer-derived molecules which elicit resistance to tumor challenges. The general approach in these experiments was to fractionate cancer-derived proteins and test them individually for their ability to immunize mice against the cancers from which the fractions were prepared.

One of the major difficulties in cancer immunotherapy has been the possibility that similar to the situation among animal cancers, each human cancer is different from all other cancers, i.e., human cancers, like cancers of experimental animals, are antigenically distinct. Clearly, there is some recent evidence for existence of common human tumor antigens (Kawakami et al., 1991, Darrow et al., 1989), and this augurs well for prospects of cancer immunotherapy. Nonetheless, in light of the overwhelming evidence from experimental and human systems, it is reasonable to assume that at the very least, human tumors would show tremendous antigenic diversity and heterogeneity.

The prospect of identification of the immunogenic antigens of individual tumors from cancer patients (or even of 'only' several different types of immunogenic antigens in case the antigens are shared), is daunting to the extent of being impractical. Numerous studies on vaccination against infectious diseases have shown that it is necessary to first identify and characterize the immunogenic antigens.

For the reasons described above, such a strategy is impractical for vaccination or other forms of immunotherapy against human cancers. Thus, there is a need to develop alternate methods for obtaining antigenic preparations which do not require such daunting identification of specific antigens from tumors of individual patients and avoids the difficulties and hazards associated with attenuation and inactivation of viruses.

SUMMARY OF THE INVENTION

This invention relates to an immunogenic composition comprising complexes of heat shock protein 70 and antigenic peptides derived from tumor cells or cells infected with a virus, bacteria or other agent. This invention also relates to a method of eliciting an immune response in a mammal comprising the steps of isolating heat shock protein 70-peptide complex from tumor cells or cells infected with a virus, bacteria or other agent and administering the heat shock protein 70-peptide complex to the mammal in an amount effective to elicit an immune response. The claimed invention provides a novel method of eliciting antigen-specific cellular immunity against tumors, endogenous antigens, bacterial and viral antigens.

This invention further relates to a method of preparing a heat shock protein 70-peptide complex capable of eliciting an immune response in a mammal comprising the steps of obtaining tumor cells from the mammal or cells which are infected with a virus, bacteria or other infectious agent, preparing an aqueous cell extract, purifying the extract through column chromatography and harvesting a heat shock protein 70-peptide complex in the absence of adenosine triphosphate (ATP).

This invention additionally relates to a method of preparing an antigenic peptide composition comprising obtaining cells from a mammal wherein the cells are tumor cells or cells infected with a virus, bacteria or other infectious agent, harvesting a heat shock protein 70-peptide complex from the cells wherein the heat shock protein 70-peptide complex is prepared in the absence of ATP and separating peptides from the heat shock protein 70-peptide complex, wherein the separated peptides are capable of eliciting an immune response in the mammal.

This invention also relates to an immunogenic composition comprising complexes of heat shock protein 70 and antigenic peptides derived from tumor cell lines or cell lines infected with a virus or bacteria. The invention further relates to a method of preparing a heat shock protein 70-peptide complex capable of eliciting an immune response in a mammal comprising preparing an aqueous cell extract from tumor cell lines or cell lines infected with a bacteria or virus, purifying the extract through column chromatography and harvesting a heat shock protein 70-peptide complex in the absence of ATP.

DETAILED DESCRIPTION OF THE PREFERRED EMBODIMENT

Figure 1A:
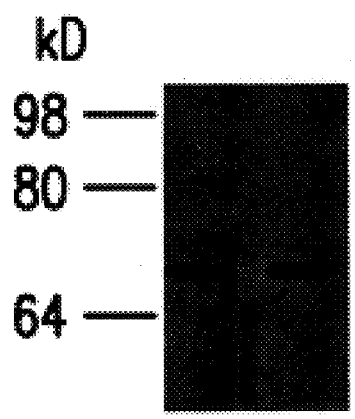
FIG. 1 depicts SDS-PAGE followed by silver staining of (a) purified hsp 70 preparations from Meth A ascitic cells and (b) immunoblot of hsp 70 preparations in (a) with anti-heat shock protein antibody.

It has been found that vaccination of mice with heat shock protein 70 (hsp 70) preparations derived from methylcholanthrene-induced sarcoma (Meth A), e.g., a hydrocarbon-induced sarcoma, but not from normal tissues renders the mice immune to a substantial challenge with Meth A sarcoma. This immunity is tumor-specific. It has also been found that hsp 70 loses its antigenicity upon treatment with ATP. Such treatment is known to result in dissociation of hsp 70 from a spectrum of peptides. Considering that there are no known differences in the structure of hsp 70 per se between normal and cancer cells, and that hsp 70 binds a wide spectrum of peptides in an ATP-dependent manner, it appears that the antigenicity of hsp 70 derives, not from hsp 70 per se, but from associated peptides. Thus, the claimed invention provides a novel method of utilizing the peptide binding property of hsp 70 comprising isolating a heat shock protein 70-peptide complex from tumor cells or cells infected with a virus, bacteria or infectious agent and administering the heat shock protein 70-peptide complex to a mammal in an amount effective to elicit an immune response. In this regard, immunization with this hsp 70-peptide complex is believed to elicit a CD4+ and CD8+ T cell response and is therefore useful in promoting cell-mediated immunity which is particularly important as a defense against viral and bacterial infections or tumors.

In addition, the present invention provides for a method for purifying hsp 70 which leaves intact the association between hsp 70 and the antigenic peptides which it "chaperones". This method, set forth in detail in the example sections which follow, may be applied to either tumor cells and virus or bacteria-infected cells to the same effect. In the case of tumor cells, hsp 70 in association with tumor-specific antigenic peptides is purified, and in the case of virus-infected cells, hsp 70 in association with viral antigenic peptides is purified, and in the case of bacteria-infected cells, hsp 70 in association with bacterial antigenic peptides is purified. In this regard, purification of the hsp 70 associated with antigenic peptides must be performed in the absence of adenosine triphosphate (ATP), which appears to displace the antigenic peptides associated with hsp 70.

The present invention further provides for the purification and isolation of antigenic peptides which are associated (or "chaperoned") by hsp 70 in virus or bacteria-infected or tumor cells. A non-denaturing method may be used to elute chaperoned peptides from the hsp 70-peptide complex described above. In a specific, non-limiting embodiment of the invention, an hsp 70-peptide complex (e.g., as prepared in the example sections which follow, or from the same methods as applied to virus or bacteria-infected cells) may be centrifuged through a CENTRICON 10 filtration assembly in order to remove any low molecular weight material loosely associated with it. The large molecular weight fraction may be recovered and analyzed by SDS-PAGE while the low molecular weight material may be analyzed by HPLC, as described infra. The hsp 70 preparation in the large molecular weight fraction may be incubated with ATP at a final concentration of about 10 mM at room temperature for 30 minutes and centrifuged through Centricon 10 as before. The two fractions may be recovered, and the ATP treatment of the large molecular weight hsp 70 fraction may be repeated two or more times. The lower molecular weight fractions may then be pooled, concentrated by evaporation in a Speed Vac and then dissolved in 0.1% trifluoroacetic acid (TFA). This material may then be applied to a VYDAC C18 packing material reverse phase HPLC column pre-equilibrated with 0.1% TFA. The bound material may then be eluted at a flow rate of about 0.8 ml/min by a linear gradient of 0 to 79.9% acetonitrile in 0.1% TFA. The ultraviolet light absorbance at 210 nm may be monitored to identify fractions containing antigenic peptide. Antigenic peptides prepared in this manner may be used in immunogenic compositions which may be used to elicit immunity in a mammal in need of such treatment. It may, in certain circumstances, be desirable to administer such peptides linked to or otherwise associated with a carrier molecule, so as to promote immunity.

The present invention also provides for immunogenic compositions which comprise either hsp 70-peptide complex or antigenic peptides. Such compositions may further comprise a suitable carrier such as phosphate-buffered saline (5 mM Na phosphate buffer, 150 mM NaCl, pH 7.1) or other physiologically compatible solution. The immunogenic composition may optionally comprise one or more adjuvants. Suitable adjuvants include, but are not limited to, pluronic tri-block copolymers, muramyl dipeptide and its derivatives, detoxified endotoxin, saponin and its derivatives such as QS-21 saponin derivative and liposomes. The present invention further envisages sustained release formulations in which antigen is released over a protracted period of time. In preferred, non-limiting embodiments of the invention, the amount of hsp 70-peptide complex administered may be about 50–1000 micrograms/kg body weight of the mammal, most preferably 100–250 micrograms/kg body weight, per immunization, and in particular, about 7.5 mg to 18.75 mg for an approximately 75 kilogram human subject. The quantities of hsp 70-peptide complex administered to human subjects may not be extrapolated directly from the amounts used in mice, as would be the case for antibiotics and metabolic drugs. Because of the immune system's ability to amplify responses extremely efficiently, smaller quantities of hsp 70-peptide complex may be required to immunize human subjects than would be expected from a direct extrapolation from mice. Further, the quantities may vary depending upon the adjuvant formulation which may be administered along with the hsp 70-peptide complex.

The immunogenic compositions of the invention may be administered in immunogenic amounts to subjects in need of such treatment using standard protocols, which would include, but not be limited to, intramuscular, subcutaneous, intradermal, intraperitoneal, intravenous, intravaginal, intrarectal, oral, sublingual, transcutaneous, and intranasal administration. It may be desirable to provide a series of immunizations in order to optimize the immune response.

The hsp 70-peptide complex can be prepared from tumor cells, including, but not limited to, adenocarcinomas, colon carcinoma, melanoma, breast carcinoma, leukemia, lymphoma, sarcomas (including fibrosarcoma and osteosarcoma), gastric carcinoma, glioblastoma, astrocytoma, bladder carcinoma, pleural mesothelioma, oat cell carcinoma, and bronchogenic carcinoma, as well as tumors induced by chemical carcinogens or radiation. Chemical carcinogens include carcinogens associated with cigarette smoking, such as hydrocarbons and carcinogenic air, food, cosmetic or other pollutants.

The hsp 70-peptide complex can also be prepared from virus-infected cells where the virus may be influenza, varicella, herpes simplex I or II, HIV-I or HIV-II, hepatitis A, B or C, adenovirus, measles, mumps, etc.

The hsp 70-peptide complex may also be prepared from bacteria-infected cells including, but not limited to, cells infected with bacteria causing tuberculosis, gonorrhea, typhoid, meningitis, osteomyelitis, meningococcal septicemia, endometritis, conjunctivitis, peritonitis, pyelonephritis, pharyngitis, septic arthritis, cellulitis, epiglottitis, salpingitis, otitis media, shigella dysentery, gastroenteritis, etc.

The hsp 70-peptide complex can also be prepared from tumor cell lines or cell lines infected with a virus or bacteria. In addition, the hsp 70-peptide complex may be prepared from viral gene transfected cells.

Immunization with an hsp 70-peptide complex offers a number of significant and unique advantages over other methods of immunization against viruses, bacteria or cancer. Hsp 70 protein-peptide complex carries a variety of immunogenic peptides derived from the cells from which it is isolated. Thus, immunization with an hsp 70-peptide complex obviates the necessity for isolation and characterization of antigenic molecules. In addition, immunization with biochemically undefined tumor or other extracts inevitably carries the risk of inoculating the mammal recipient with potentially transforming or immunosuppressive agents such as transforming DNA or tumor growth factor beta (TGFB). Immunization with purified hsp 70-peptide complex eliminates these risks. Moreover, it has been found that immunization with hsp 70-peptide complex elicits significant tumor immunity without the use of adjuvants. While adjuvants which may further potentiate the immunity elicited by the hsp 70-peptide complex may be sought, their availability is not a pre-condition for a significant protective response. This is a very significant advantage for human subjects because the availability of adjuvants for human use is rather limited.

The claimed invention is one of the very few methods of vaccination which elicit cellular immunity without the use of live (attenuated or otherwise) agents. The immunogenic compositions prepared from hsp 70-peptide complex in accordance with the invention are an ideal vaccination means for infections for which either the protective immunogenic epitopes are yet undefined, where binding to a single epitope may not be sufficient for eliciting immunity, or where the infectious agent is so highly variable (in a population, season or individual-specific manner) that the prospect of identifying the immunogenic epitopes for each variant is simply impractical. In addition, the hsp 70-peptide complex has a number of different peptides associated with it, which potentially may include a number of different antigens capable of binding to a variety of epitopes. As hsp 70 molecules are non-polymorphic, i.e., show no allelic diversity, even though there are several families, they are capable of binding the entire spectrum of antigenic peptides regardless of the MHC haplotype of a given cell. Thus, an hsp 70-peptide complex isolated from cells of any given haplotype may be used to vaccinate individuals of other haplotypes. Moreover, the recent recurrence of antibiotic-resistant strains of a number of infectious diseases presently treated by antibiotics and metabolic drugs such as tuberculosis, highlights the need for a general method as provided by the claimed invention which can be rapidly mobilized against a variant without having to define its molecular characteristics.

The novel ability of hsp 70-peptide complex in accordance with the invention to elicit an immune response is illustrated in the following examples.

EXAMPLE 1

Preparation of Purified hsp 70-Peptide Complex

BALB/cJ mice (viral antigen free) were obtained from Jackson laboratories and were maintained in virus-free mouse facilities. Tumor cells were injected intraperitoneally in 0.2 ml volume as described in Srivastava et al., Proc. Natl. Acad. Sci., vol. 83, pp. 3407–3411 (May, 1986). Meth A ascites cells were collected after 7 days and were suspended at a density of $10^6$ cell/ml in Dulbecco's Modified Eagles Medium (DMEM) without methionine, containing 10% dialyzed fetal calf serum. Cells were cultured in the absence of methionine for 4 hours in order to deplete methionine pools. They were then re-suspended in fresh methionine-free medium containing TRANS-LABEL (which contains $^{35}$S-methionine 100 $\mu$Ci/ml) for one hour and harvested and a 40 ml Meth A cell pellet was derived. The 40 ml Meth A cell pellet was homogenized in 120 ml hypotonic buffer (30 mM $NaHCO_3$, pH 7.1, 0.5 mM phenyl methyl sulfonyl fluoride (PMSF)) and a 100,000 g supernatant obtained. This was applied to a Concanavalin A-Sepharose column in presence of 2 mM $Ca^{++}$ and the unbound material was dialyzed against 10 mM tris-acetate pH 7.5, 10 mM NaCl, 0.1 mM EDTA. This fraction was resolved on a MONO Q ion exchange Pharmacia FPLC system equilibrated with 20 mM tris-acetate pH 7.5, 20 mM NaCl, 0.1 mM EDTA, 15 mM 2-mercaptoethanol. The proteins were eluted by a 20 mM to 500 mM NaCl gradient. Fractions (1 ml) were collected and tested by SDS-PAGE. Hsp 70 containing fractions were identified by molecular weight and by immunoblotting with anti-hsp 70 monoclonal antibody.

Figure 1B:
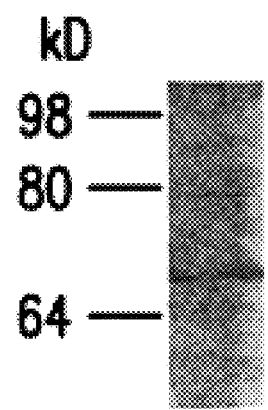

The hsp 70 containing fractions were pooled and precipitated with increasing saturation levels of ammonium sulfate. Hsp 70 was precipitated at 50%–70% ammonium sulfate saturation. The later fractions in this process were shown to be homogeneous by silver staining and were used for immunization of mice. The left lane in FIG. 1(a) shows the SDS-PAGE profile of a purified hsp 70 fraction. The purified hsp 70 fraction obtained in the absence of ATP, shown in the left lane of FIG. 1(a), was immunoblotted on nitrocellulose and probed with a group hsp 70 monoclonal antibody N27F3-4 (Stress Gen product # SPA-820) (FIG. 1(b)). The right lane in FIG. 1(a) is the SDS-PAGE profile for precipitated fractions collected as described above but which were additionally passed through an ATP-agarose column and eluted in the presence of 3 mM ATP.

For purification of hsp 70 from liver, the 100,000 g supernatant was first applied to a Blue Sepharose column in order to remove albumin.

EXAMPLE 2

Tumor Immunogenicity of hsp 70-Peptide Complex

Figure 2A:
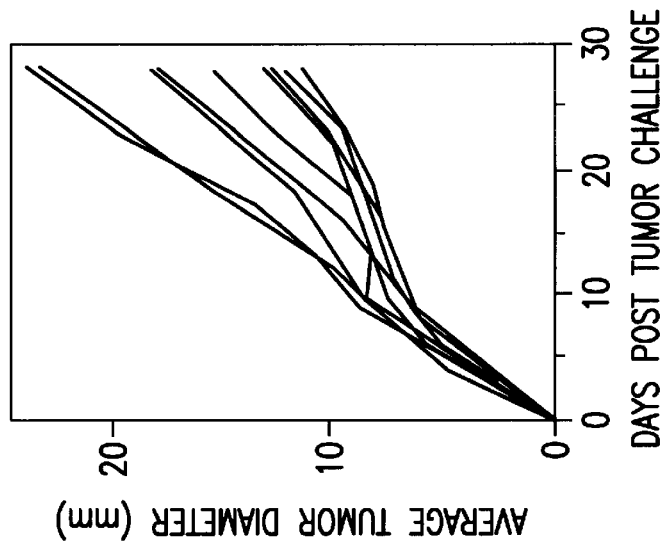
FIG. 2 depicts kinetics of tumor growth in mice immunized with 9 $\mu$g, 6 $\mu$g, and 3 $\mu$g of hsp 70-peptide complex.
Figure 2B:
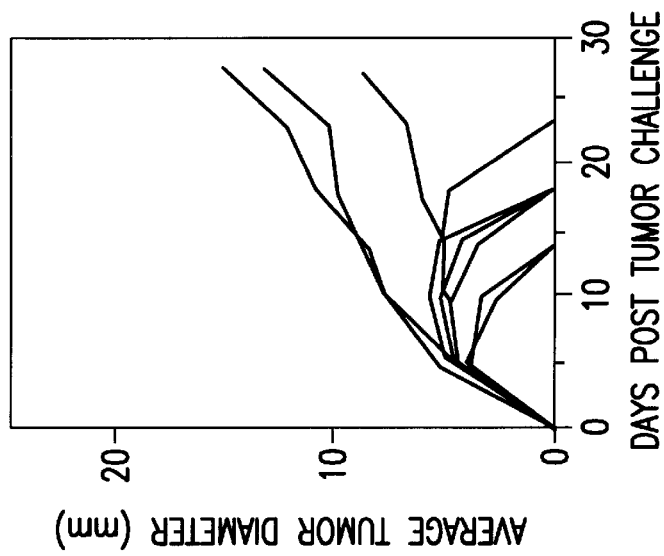
Figure 2C:
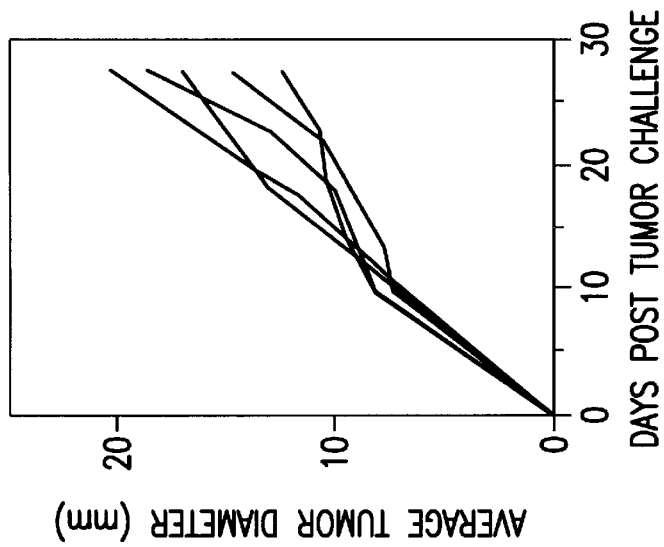
Figure 3A:
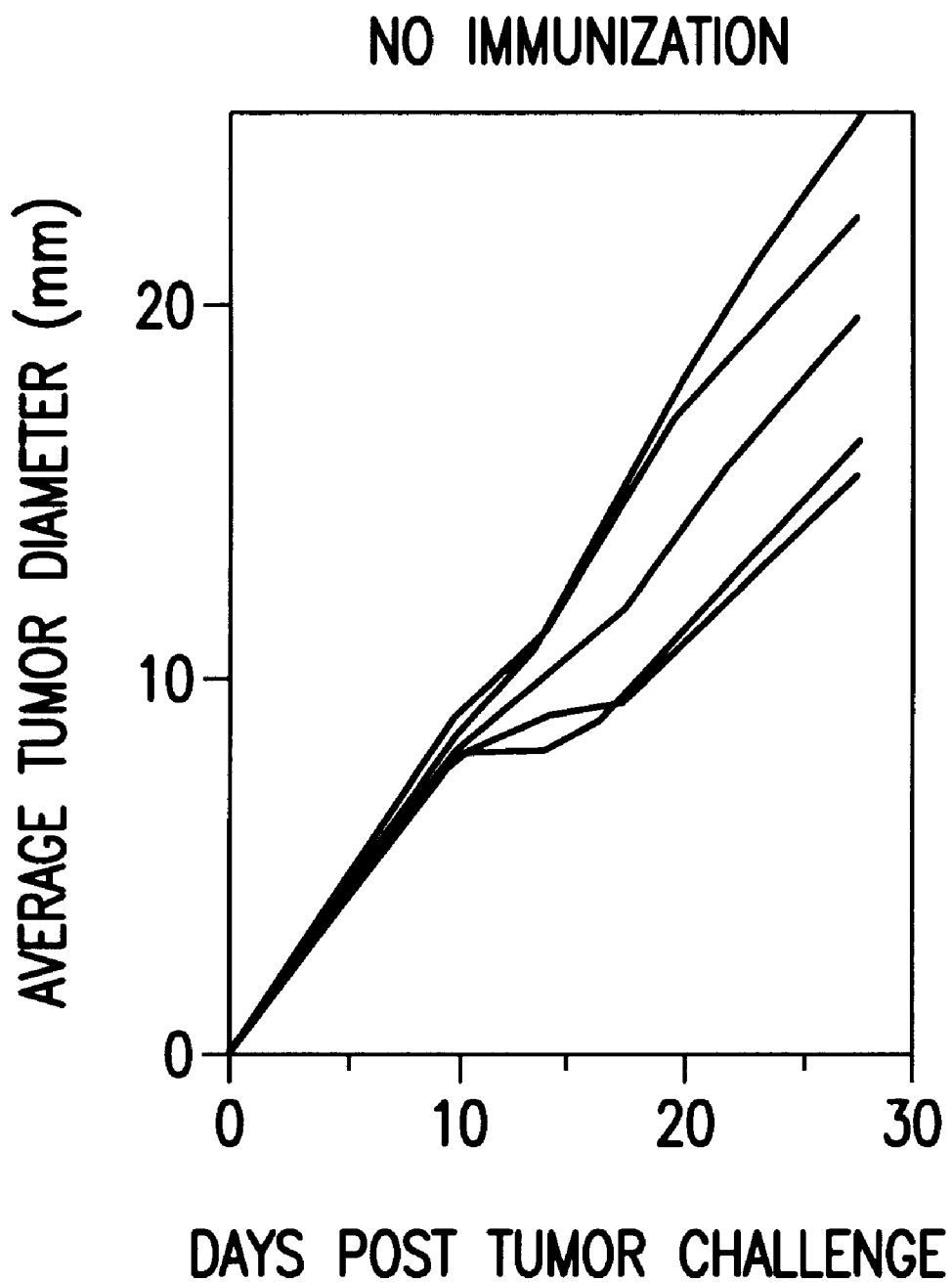
FIG. 3 depicts kinetics of tumor growth in mice immunized with hsp 70 preparations purified by conventional chromatography and by ATP-agarose chromatography.
Figure 3D:
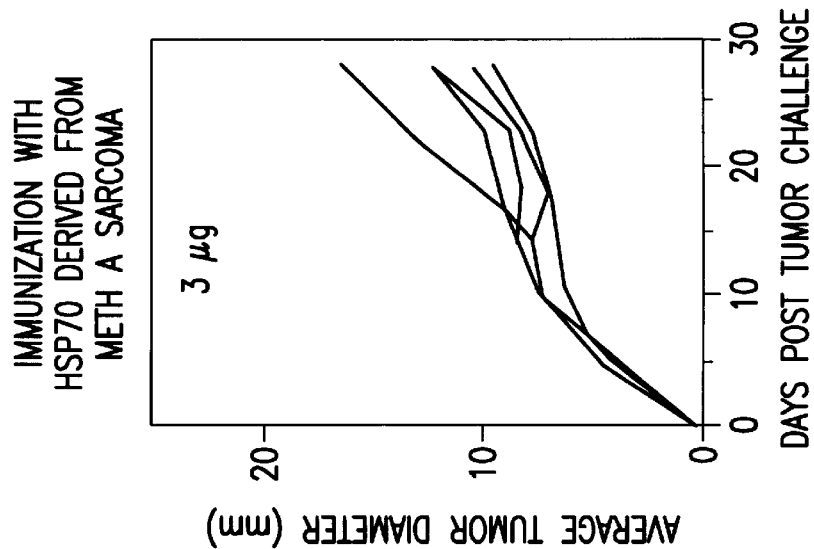
Figure 3C:
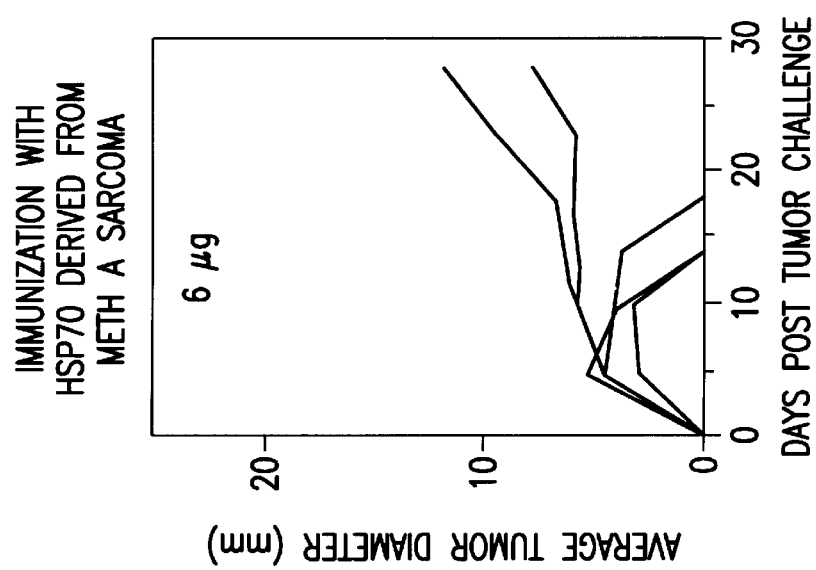
Figure 3B:
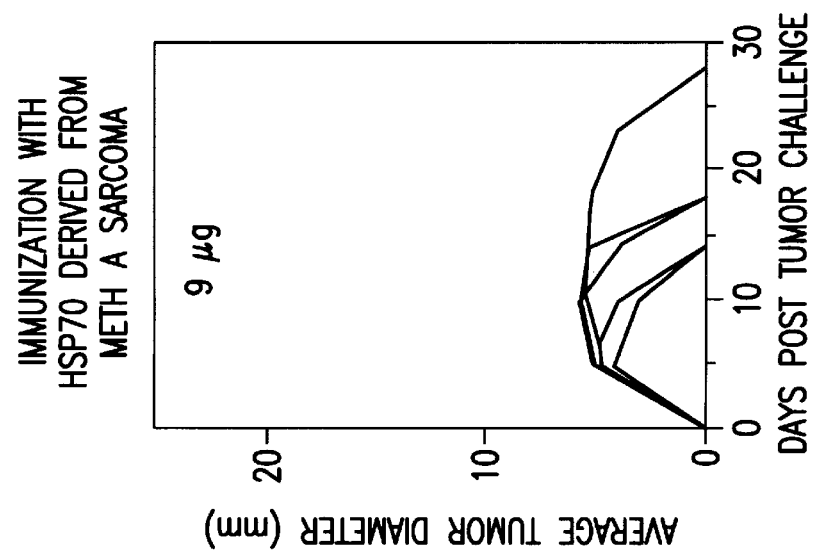

The biochemically homogeneous hsp 70 preparations obtained in the absence of ATP from the BALB/cJ fibrosarcoma Meth A or from normal tissue, as described above, were used to immunize BALB/cJ mice twice at weekly intervals. Immunization was carried out in 200 $\mu$l volume subcutaneously. Mice were challenged with 70,000 live Meth A cells intradermally one week after the second immunization. The kinetics of tumor growth is shown in FIG. 2. Each line represents the kinetics of tumor growth in a single mouse. Tumors grew progressively in all unimmunized mice, but there was significant protection from tumor growth in hsp 70-peptide complex immunized mice. This effect was dose-dependent. Two injections of 3 $\mu$g of hsp 70-peptide complex each did not immunize mice against Meth A, while two injections of 9 $\mu$g each conferred complete protection to all vaccinated mice. As hsp 70 is a ubiquitous protein, present in normal tissues as well as in tumors, hsp 70 preparations from normal liver and spleens were tested for immunogenicity in the same manner. No protective effect of hsp 70 derived from normal tissues was observed at any of the three doses tested (see FIG. 2).

EXAMPLE 3

Tumor Specificity of Meth A Derived hsp 70-Peptide Complex

In order to determine the tumor specificity of the Meth A derived hsp 70-peptide complex, mice were challenged with antigenically distinct methylcholanthrene-induced BALB/cJ sarcomas CMS4 and CMS5 in accordance with the procedure described in Example 2. The results are shown in Table 1.

TABLE 1

Specificity of immunity elicited by immunity with hsp 70 derived from Meth A sarcoma

| Mice | Number of tumor cells used for challenge | Tumor used for challenge | | |
|---|---|---|---|---|
| | | Meth A | CMS5 | CMS4 |
| Immunologically naive mice | $5 \times 10^4$ | 5/5[1] | 4/5 | N.D. |
| | $1 \times 10^5$ | 5/5 | 5/5 | 5/5 |
| Mice immunized with Meth A hsp 70[2] | $5 \times 10^4$ | 0/5 | 5/5 | N.D. |
| | $5 \times 10^5$ | 0/5 | 5/5 | 5/5 |

[1] Number of mice in which the tumors grew per total number of mice challenged.
[2] Mice were immunized with 10 μg of Meth A hsp 70, twice at weekly intervals and challenged with 50,000 Meth A cells. The mice rejected the Meth A sarcoma and were challenged with other sarcomas.

As can be seen from Table 1, mice immunized with Meth A derived hsp 70-peptide complex remained sensitive to challenge with antigenically distinct methylcholanthrene-induced BALB/cJ sarcomas CMS4 and CMS5.

EXAMPLE 4

Immunogenicity of hsp 70 Purified in the Presence of ATP

The hsp 70 purified in the presence of 3 mM ATP as described in Example 1 was tested for immunogenicity in accordance with the procedure described in Example 2. The results are shown in FIG. 3. The Figure showed tumor growth for mice not immunized (FIG. 3(a)), tumor growth for mice immunized with Meth A derived hsp 70-peptide complex purified in the absence of ATP (FIG. 3(b)), and in the presence of ATP (i.e., peptide depleted) (FIG. 3(c)). Mice vaccinated with Meth A derived hsp 70-peptide complex purified in the absence of ATP were significantly protected against tumor challenge, but the mice vaccinated with the ATP-eluted Meth A derived hsp 70-peptide complex were not.

These data suggest that the immunogenicity of the Meth A derived hsp 70-peptide complex derives from the antigenic peptides associated with it. The peptides are most likely derived from cellular proteins by proteolytic degradation during antigen presentation by major histocompatibility complex (MHC) Class I and Class II proteins. The hsp 70 molecules encounter peptides in the endoplasmic reticulum, endosomes and in the cytosol. While not wishing to be confined to a specific theory, the peptides generated in tumor cells must clearly differ from those generated in normal tissues because of the tumor associated mutations, and may therefore result in the difference in the antigenicity of tumor versus normal cell derived hsp 70-peptide complex.

EXAMPLE 5

Tumor Immunogenicity of hsp 70-Peptide Complex Derived from Cell Lines

In order to determine the tumor immunogenicity of an hsp 70-peptide complex, cells from the CMS4 cell line were cultured in 10% fetal calf serum in Roswell Park Memorial Institute (RPMI) medium. A 4 ml CMS4 cell pellet was derived. The 4 ml CMS4 cell pellet was homogenized in 12 ml hypotonic buffer (30 mM $NaHCO_3$, pH 7.1, 0.5 mM PMSF) and a 100,000 g supernatant obtained. This was applied to a Concanavalin A-Sepharose column in presence of 2 mM $Ca^{++}$ and the unbound material was dialyzed against 10 mM tris-acetate pH 7.5, 10 mM NaCl, 0.1 mM EDTA. This fraction was resolved on a Mono Q Pharmacia FPLC system equilibrated with 20 mM tris-acetate pH 7.5, 20 mM NaCl, 0.1 mM EDTA, 15 mM 2-mercaptoethanol. The proteins were eluted by a 20 mM to 500 mM NaCl gradient. Fractions (1 ml) were collected and tested by SDS-PAGE. Hsp 70 containing fractions were identified by molecular weight and by immunoblotting with anti-hsp 70 monoclonal antibody. The hsp 70 containing fractions were pooled and precipitated with increasing saturation level of ammonium sulfate. Hsp 70 was precipitated at 50%–70% ammonium sulfate saturation. The later fractions in this process were shown to be homogeneous by silver staining and were used for immunization of mice.

Figure 4A:
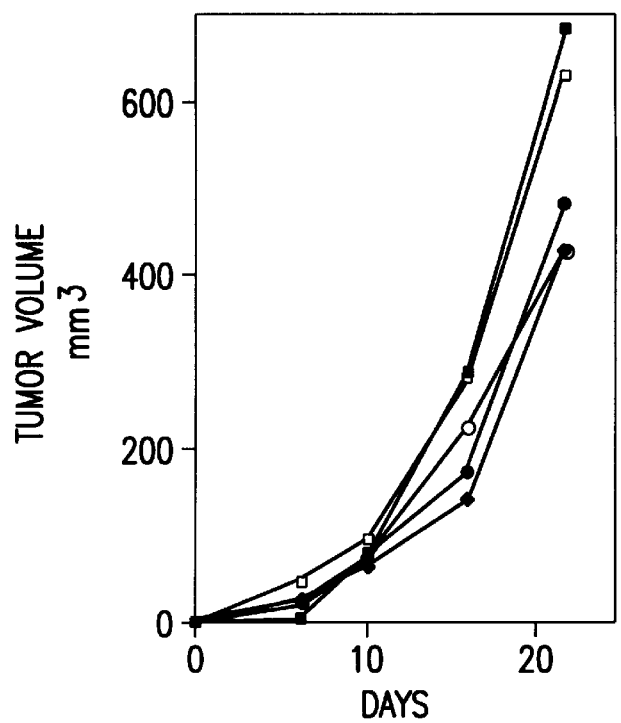
FIG. 4 depicts kinetics of growth of the CMS4 tumor in mice immunized with (a) Meth A ascitic cell lysate or (b) hsp 70-peptide complex derived from CMS4 cell line.
Figure 4B:
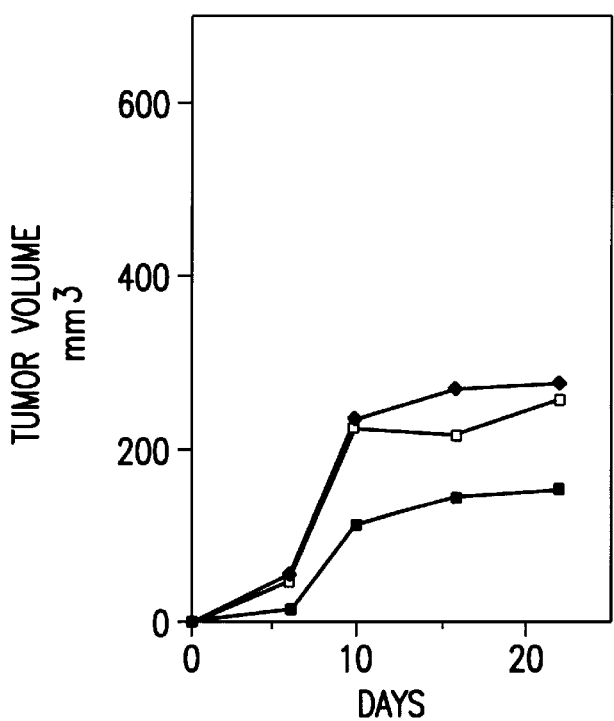

The purified hsp 70 preparation obtained from the CMS4 cell line as described above or lysate from Meth A cells were used to immunize BALB/cJ mice. The mice were immunized with 9 μg of either the purified hsp 70 preparation obtained from the CMS4 cell line or Meth A lysate twice at weekly intervals. Immunization was carried out in 200 μl volume subcutaneously. Mice were challenged with 50,000 live CMS4 cells intradermally one week after the second immunization. The kinetics of tumor growth is shown in FIG. 4. Each line represents the kinetics of tumor growth in a single mouse. Tumors grew progressively in mice immunized with the Meth A lysate (FIG. 4(a)), but there was significant protection from tumor growth in mice immunized with hsp 70-peptide complex derived from the CMS4 cell line (FIG. 4(b)).

Although the invention has been described herein with reference to specific embodiments, many modifications and variations therein will readily occur to those skilled in the art. Accordingly, all such variations are included within the intended scope of the invention.

I claim:

1. A method of preparing a purified non-covalent heat shock protein 70-peptide complex capable of eliciting an immune response in a mammal comprising the step of:
   purifying a non-covalent heat shock protein 70-peptide complex from mammalian tumor tissue or mammalian cells infected with a virus, bacteria, or other infectious agent in the absence of ATP, in an amount capable of eliciting an immune response in a mammal.

2. The method according to claim 1 wherein the non-covalent heat shock protein 70-peptide complex is purified from a cell line infected with a virus, bacteria or other infectious agent.

3. The method according to claim 1 wherein the non-covalent heat shock protein 70-peptide complex is purified from bacteria-infected cells.

4. The method according to claim 3 wherein the non-covalent heat shock protein 70-peptide complex is purified from a cell line infected with a bacteria.

5. The method according to claim 3 wherein the cells are infected with a bacteria causing a disease selected from the group consisting of tuberculosis, gonorrhea, typhoid, meningitis, osteomyelitis, meningococcal septicemia, endometritis, conjunctivitis, peritonitis, pyelonephritis, pharyngitis, septic arthritis, cellulitis, epiglottitis, salpingitis, otitis media, shigella dysentery, and gastroenteritis.

6. The method according to claim 1 wherein the cells are virus-infected cells.

7. The method according to claim 6 wherein the cells are from a cell line infected with a virus.

8. The method according to claim 1 wherein the cells are viral gene transfected cells.

9. The method according to claim 6 wherein the virus is selected from the group consisting of influenza, varicella, herpes simplex I, herpes simplex II, HIV-I, HIV-II, hepatitis A, hepatitis B, hepatitis C, adenovirus, measles and mumps.

10. The method according to claim 1 wherein the non-covalent heat shock protein 70-peptide complex is purified from tumor tissue.

11. The method according to claim 10 wherein the tumor is selected from the group consisting of adenocarcinoma, colon carcinoma, melanoma, breast carcinoma, leukemia, lymphoma, sarcoma, gastric carcinoma, glioblastoma, astrocytoma, bladder carcinoma, pleural mesothelioma, oat cell carcinoma, and bronchogenic carcinoma.

12. The method according to claim 10 wherein the tumor is induced by a chemical carcinogen.

13. The method according to claim 12 wherein the tumor is a hydrocarbon-induced tumor.

14. The method according to claim 13 wherein the tumor is a methylcholanthrene-induced tumor.

15. A method of preparing a purified antigenic peptide composition comprising the steps of:
purifying non-covalent heat shock protein 70-peptide complexes from mammalian tumor cells or mammalian cells infected with a virus, bacteria, or other infectious agent in the absence of ATP;
separating peptides from the non-covalent heat shock protein 70-peptide complexes; and
recovering the separated peptides, wherein the separated peptides are capable of eliciting an immune response in a mammal.

16. The method of preparing an antigenic peptide composition according to claim 15 wherein the cells are from a tumor cell line or a cell line infected with a virus, bacteria or other infectious agent.

17. The method of preparing an antigenic peptide composition according to claim 15 wherein the cells are bacteria-infected cells.

18. The method of preparing an antigenic peptide composition according to claim 17 wherein the cells are from a cell line infected with a bacteria.

19. The method of preparing an antigenic peptide composition according to claim 17 wherein the cells are infected with bacteria causing a disease selected from the group consisting of tuberculosis, gonorrhea, typhoid, meningitis, osteomyelitis, meningococcal septicemia, endometritis, conjunctivitis, peritonitis, pyelonephritis, pharyngitis, septic arthritis, cellulitis, epiglottitis, salpingitis, otitis media, shigella dysentery, and gastroenteritis.

20. The method of preparing an antigenic peptide composition according to claim 15 wherein the cells are virus-infected cells.

21. The method of preparing an antigenic peptide composition according to claim 20 wherein the cells are from a cell line infected with a virus.

22. The method of preparing an antigenic peptide composition according to claim 15 wherein the cells are viral gene transfected cells.

23. The method of preparing an antigenic peptide composition according to claim 20 wherein the virus is selected from the group consisting of influenza, varicella, herpes simplex I, herpes simplex II, HIV-I, HIV-II, hepatitis A, hepatitis B, hepatitis C, adenovirus, measles and mumps.

24. The method of preparing an antigenic peptide composition according to claim 15 wherein the cells are tumor cells.

25. The method of preparing an antigenic peptide composition according to claim 24 wherein the cells are from a tumor cell line.

26. The method of preparing an antigenic peptide composition according to claim 24 wherein the tumor cells are selected from the group consisting of adenocarcinomas, colon carcinoma, melanoma, breast carcinoma, leukemia, lymphoma, sarcoma, gastric carcinoma, glioblastoma, astrocytoma, bladder carcinoma, pleural mesothelioma, oat cell carcinoma, and bronchogenic carcinoma.

27. The method of preparing an antigenic peptide composition according to claim 24 wherein the tumor is induced by a chemical carcinogen.

28. The method of preparing an antigenic peptide composition according to claim 27 wherein the tumor is a hydrocarbon-induced tumor.

29. The method of preparing an antigenic peptide composition according to claim 28 wherein the tumor is a methylcholanthrene-induced tumor.

30. The method according to claim 3, 6, 15, 17, 20 or 24 wherein the cells are human cells.

31. The method according to claim 1 wherein the tissue is human tissue and the cells are human cells.

32. The method according to claim 1 wherein said purifying step comprises subjecting an aqueous extract of the cells to column chromatography.

33. The method according to claim 30 wherein said purifying step comprises subjecting an aqueous extract of the cells to column chromatography.

34. The method according to claim 15 wherein said purifying step comprises subjecting an aqueous extract of the cells to column chromatography.

35. The method according to claim 31 wherein said purifying step comprises subjecting an aqueous extract of the cells to column chromatography.

36. The method according to claim 10 wherein the tissue is human tissue.

* * * * *